United States Patent
Kondo et al.

(10) Patent No.: US 6,960,691 B2
(45) Date of Patent: Nov. 1, 2005

(54) PRODUCTION PROCESS FOR HALOGENATED AROMATIC METHYLAMINE

(75) Inventors: Hideyuki Kondo, Kawasaki (JP); Yuseki Suyama, Kawasaki (JP); Kohei Morikawa, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 187 days.

(21) Appl. No.: 10/344,263

(22) PCT Filed: Jun. 17, 2002

(86) PCT No.: PCT/JP02/06008

§ 371 (c)(1),
(2), (4) Date: Feb. 10, 2003

(87) PCT Pub. No.: WO02/102760

PCT Pub. Date: Dec. 27, 2002

(65) Prior Publication Data

US 2003/0158444 A1   Aug. 21, 2003

Related U.S. Application Data

(60) Provisional application No. 60/301,144, filed on Jun. 28, 2001.

(30) Foreign Application Priority Data

Jun. 18, 2001 (JP) .......................... 2001-183006
Apr. 18, 2002 (JP) .......................... 2002-115549

(51) Int. Cl.$^7$ .......................................... C07C 211/27
(52) U.S. Cl. ................. 564/305; 564/1; 564/336; 564/374; 564/375; 564/377
(58) Field of Search .......................... 564/336

(56) References Cited

U.S. PATENT DOCUMENTS 3,412,174 A * 11/1968 Kroll .................. 585/277
5,874,625 A * 2/1999 Elsasser ............. 564/490
6,452,056 B1 * 9/2002 Kawanobe et al. ...... 568/700

FOREIGN PATENT DOCUMENTS

| EP | 1 050 527 | 11/2000 |
|---|---|---|
| EP | 1 114 809 | 7/2001 |
| GB | 810530 | 3/1959 |
| GB | 852972 | 11/1960 |
| GB | 1149251 | 4/1969 |
| GB | 2 120 666 A * | 5/1983 |
| GB | 2 120 666 | 12/1983 |
| JP | 4-14096 B2 | 3/1992 |
| WO | WO 00/17138 | 3/2000 |
| WO | WO 02/02504 | 1/2002 |
| WO | WO 02/34706 | 5/2002 |

OTHER PUBLICATIONS

Rylander, Paul N.: "Hydrogenation Methods." 1985, Academic Press, London XP002215109 p. 6, p. 95–98.
Database WPI Section Ch, Week 199315, Derwent Publications Ltd., London, GB; AN 1993–121324 XP002215110 for JP 05–058965 (Mitsui Toatsu Chem Inc), Mar. 9, 1993.

* cited by examiner

Primary Examiner—Samuel Barts
Assistant Examiner—Lansana Nyalley
(74) Attorney, Agent, or Firm—Sughrue Mion, PLLC

(57) ABSTRACT

The invention intends to provide means for producing halogenated aromatic methylamine useful as an intermediate in the production of agrochemical or medical preparations, by an industrially advantageous method.

The process according to the present invention for producing halogenated aromatic methylamine is characterized by comprising hydrogen-reducing a halogenated aromatic nitrile represented by formula (1):

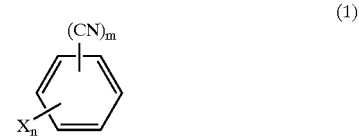

(1)

(wherein X represents a chlorine atom or a fluorine atom, m represents an integer of 1 to 5, n represents an integer of 1 to 5, $m+n \leq 6$, and when n is 2 or more, each X may be the same or different) using a hydrogenating catalyst in the presence of an organic acid in a solvent to produce a halogenated aromatic methylamine represented by formula (2):

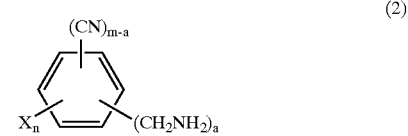

(2)

(wherein X, m and n have the same meanings as defined above, and a represents an integer of 1 to m).

19 Claims, No Drawings

PRODUCTION PROCESS FOR HALOGENATED AROMATIC METHYLAMINE

CROSS REFERENCES OF RELATED APPLICATION

This application is an application filed under 35 U.S.C. §111(a) claiming benefit pursuant to 35 U.S.C. §119(e) (1) of the filing date of Provisional Application No. 60/301,144 filed on Jun. 28, 2001 pursuant to 35 U.S.C. §111(b).

TECHNICAL FIELD

The present invention relates to a novel production process for a halogenated aromatic methylamine which is useful as an intermediate in the production of an agrochemical or pharmaceutical compound or the like. In particular, 2,3,5,6-tetrafluoroxylylenediamine and 2,3,4,6-tetrafluoroxylylenediamine are useful as an intermediate in the production of cyclopropanecarboxylic acid esters having excellent insecticidal activity.

BACKGROUND ART

A large number of methods for producing aromatic methylamines by hydrogenating an aromatic nitrile are known. For example, British Patents 810530, 852972 and 1149251 disclose a method of hydrogenating terephthalonitrile in the presence of ammonia to produce xylylenediamine. However, this method is not suitable for the production of a compound such as halogenated aromatic methylamine, which involves occurrence of a nucleophilic substitution reaction of a halogen atom by an amino group as a side reaction, though the production of a secondary amine as a by-product can be prevented to a certain extent.

With respect to the method for producing halogenated aromatic methylamines, for example, JP-B-4-14096/1992 (the term "JP-B" as used herein means an "examined Japanese patent publication") describes a method for producing halogenated xylylenediamine by reacting halogenated terephthalonitrile in the presence of a hydrogenation catalyst under inorganic acidic conditions. However, this method has a problem in that since the acid used is a strong acid such as sulfuric acid, a metal which readily dissolves under acidic conditions, such as nickel or cobalt, cannot be used as the catalyst and expensive palladium is used.

PROBLEMS TO BE SOLVED BY THE INVENTION

One of the objects of the present invention is to provide a process for producing a halogenated aromatic methylamine useful as an intermediate in the production of an agrochemical or pharmaceutical compound or the like.

One of the objects of the present invention is to provide an industrially advantageous process for producing a halogenated aromatic methylamine.

DISCLOSURE OF INVENTION

The present inventors have found that by reducing a halogenated aromatic nitrile represented by formula (1):

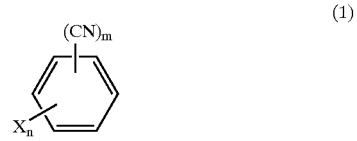

(wherein X represents a chlorine atom or a fluorine atom, m represents an integer of 1 to 5, n represents an integer of 1 to 5, m+n≦6, and when n is 2 or more, each X may be the same or different) in the presence of an organic acid in a solvent, a halogenated aromatic methylamine represented by formula (2):

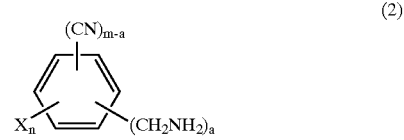

(wherein X, m and n have the same meanings as defined above, and a represents an integer of 1 to m) can be produced in a high yield. The present invention has been accomplished based on this finding.

Since an organic acid is used, a metal which readily dissolves in a strong acid, such as nickel or cobalt, can be used as the catalyst. Furthermore, the amino group of an amine produced by the above-described reaction is formed into an organic acid salt, so that a side reaction such as addition reaction of the amino group to a nitrile group or substitution reaction of a halogen atom by the amino group can be inhibited.

The present invention relates to the following matters.

[1] A process for producing a halogenated aromatic methylamine, comprising hydrogen-reducing a halogenated aromatic nitrile represented by formula (1):

(wherein X represents a chlorine atom or a fluorine atom, m represents an integer of 1 to 5, n represents an integer of 1 to 5, m+n≦6, and when n is 2 or more, each X may be the same or different) using a hydrogenating catalyst in the presence of an organic acid in a solvent to produce a halogenated aromatic methylamine represented by formula (2):

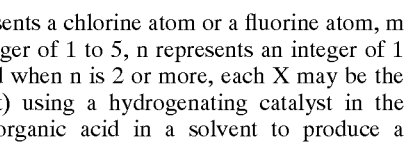

(wherein X, m and n have the same meanings as defined above, and a represents an integer of 1 to m).

[2] The production process for a halogenated aromatic methylamine as described in [1], wherein the halogenated aromatic nitrile represented by formula (1) is tetrafluoroterephthalonitrile or tetrafluoroisophthalonitrile and the halogenated aromatic methylamine represented by formula (2) is 2,3,5,6-tetrafluoroxylylenediamine or 2,3,4,6-tetrafluoroxylylenediamine.

[3] The production process for a halogenated aromatic methylamine as described in [1] or [2], wherein the solvent is a sole or combined solvent containing at least one member selected from the group consisting of aromatic hydrocarbons, aliphatic hydrocarbons, alcohols, ethers, esters and water.

[4] The production process for a halogenated aromatic methylamine as described in [1] or [2], wherein the solvent is a sole or combined solvent containing at least one member selected from the group consisting of benzene, toluene, xylene, ethylbenzene, hexane, cyclohexane, methanol, ethanol, propanol, tetrahydrofuran, dioxane, dioxolane, ethyl acetate and water.

[5] The production process for a halogenated aromatic methylamine as described in [3] or [4], wherein the solvent is a combined solvent of water and an organic solvent which is not completely miscible with water.

[6] The production process for a halogenated aromatic methylamine as described in [5], wherein the organic solvent which is not completely miscible with water is an aromatic hydrocarbon.

[7] The production process for a halogenated aromatic methylamine as described in [6], wherein the aromatic hydrocarbon is toluene, xylene or ethylbenzene.

[8] The production process for a halogenated aromatic methylamine as described in [1] or [2], wherein the solvent is water.

[9] The production process for a halogenated aromatic methylamine as described in any one of [1] to [8], wherein the organic acid is at least one member selected from the group consisting of formic acid, acetic acid and propionic acid.

[10] The production process for a halogenated aromatic methylamine as described in any one of [1] to [9], wherein the catalyst contains at least one metal selected from the group consisting of nickel, palladium, platinum, ruthenium, cobalt and copper.

[11] The production process for a halogenated aromatic methylamine as described in any one of [1] to [9], wherein the catalyst is sponge nickel or sponge cobalt.

[12] The production process for a halogenated aromatic methylamine as described in [11], wherein the catalyst is sponge nickel.

[13] The production process for a halogenated aromatic methylamine as described in [12], wherein the sponge nickel is modified with metal other than nickel.

[14] The production process for a halogenated aromatic methylamine as described in [13], wherein the sponge nickel which is modified with molybdenum.

[15] The production process for a halogenated aromatic methylamine as described in any one of [1] to [14], wherein the catalyst is used after pre-treatment in solvent under hydrogen atmosphere at 40° C. or less.

[16] The production process for a halogenated aromatic methylamine as described in any one of [1] to [9], wherein the catalyst is a supported palladium.

[17] The production process for a halogenated aromatic methylamine as described in any one of [1] to [16], wherein the amount of the solvent used is from 1 to 20 times in mass based on the halogenated aromatic nitrile.

[18] The production process for a halogenated aromatic methylamine as described in any one of [1] to [17], wherein the amount of the organic acid used is from 50 to 500 mol % based on the nitrile group of the halogenated aromatic nitrile.

[19] The production process for a halogenated aromatic methylamine as described in any one of [1] to [18], wherein the amount of the catalyst used is from 0.01 to 1 times in mass based on the halogenated aromatic nitrile.

[20] The production process for a halogenated aromatic methylamine as described in any one of [1] to [18], wherein the hydrogen reduction is performed at a reaction temperature of room temperature to 100° C. under a hydrogen partial pressure of 0.1 to 5 MPa.

[21] A halogenated aromatic methylamine represented by formula (2) obtained by the production process as described in any one of [1] to [20]:

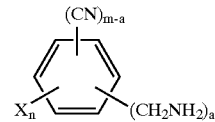
(2)

wherein X represents a chlorine atom or a fluorine atom, m represents an integer of 1 to 5, n represents an integer of 1 to 5, m+n≦6, and when n is 2 or more, each X may be the same or different, and a represents an integer of 1 to m.

[22] A catalyst used for producing a halogenated aromatic methylamine represented by formula (2) from a halogenated aromatic nitrile represented by formula (1):

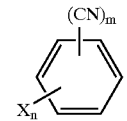
(1)

(wherein X represents a chlorine atom or a fluorine atom, m represents an integer of 1 to 5, n represents an integer of 1 to 5, m+n≦6, and when n is 2 or more, each X may be the same or different);

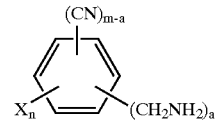
(2)

(wherein X, m and n have the same meanings as defined above, and a represents an integer of 1 to m).

MODE FOR CARRYING OUT THE INVENTION

The present invention is described in detail below. The halogenated aromatic nitrites used as a starting material of the present invention are commercially available and can be easily purchased. In formula (1), the nitrile group and the halogen each is not limited on the bonding number and the bonding position. Examples of the halogen include chlorine and fluorine.

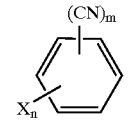
(1)

(wherein X represents a chlorine atom or a fluorine atom, m represents an integer of 1 to 5, n represents an integer of 1 to 5, m+n≦6, and when n is 2 or more, each X may be the same or different).

Specific examples of the halogenated aromatic nitriles represented by formula (1) include tetrafluorophthalonitrile, tetrafluoroisophthalonitrile, tetrafluoroterephthalonitrile, pentafluorobenzonitrile, 2,3,5,6-tetrafluorobenzonitrile, 2,3,4,6-tetrafluorobenzonitrile, 2,3,4,5-tetrafluorobenzonitrile, 2,4,6-trifluoro-5-chloroisophthalonitrile, tetrachlorophthalonitrile, tetrachloroisophthalonitrile and tetrachloroterephthalonitrile.

In the present invention, the halogenated aromatic nitrile represented by formula (1) is reduced in the presence of an organic acid in a solvent using a hydrogenation catalyst, whereby a halogenated aromatic methylamine represented by formula (2) can be obtained.

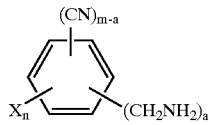

(2)

(wherein X represents a chlorine atom or a fluorine atom, m represents an integer of 1 to 5, n represents an integer of 1 to 5, m+n≦6, and when n is 2 or more, each X may be the same or different, and a represents an integer of 1 to m).

The organic acid for use in the present invention is a carboxylic acid and examples thereof include formic acid, acetic acid, propionic acid, oxalic acid, citric acid, glycolic acid and benzoic acid. Among these, preferred are formic acid, acetic acid and propionic acid. These organic acids may be used individually or in combination of two or more thereof. The amount of the organic acid used is from 50 to 500 mol %, preferably from 100 to 300 mol %, based on the nitrile group of the halogenated aromatic nitrile represented by formula (1) The organic acid may be added in one lot at the initiation of reaction or may be continuously or intermittently added with the progress of the reaction.

The hydrogenating catalyst used in the present invention is a metal catalyst containing at least one member selected from the group consisting of cobalt, iron, nickel, platinum and palladium. The catalyst may be a metal as it is or may be in the form of a supported catalyst. Examples of the support for the supported catalyst include activated carbon, silica and alumina. The catalyst is preferably, for example, sponge nickel or sponge cobalt. Further, in the present invention, modified sponge catalyst may be used. Modified sponge catalyst is obtained by modifying nickel or cobalt with other metal or metal oxide than nickel or cobalt. For instance, sponge nickel catalyst modified with molybdenum is exemplified.

The amount of the catalyst used is from 0.01 to 1 times in mass, more preferably from 0.02 to 0.5 times in mass, based on the halogenated aromatic nitrile represented by formula (1) Activity of the catalyst can be enhanced by pre-treating the catalyst in solvent under hydrogen atmosphere. Temperature of the pre-treatment is 100° C. or less, preferably 40° C. or less. The pressure at this time is, in terms of the hydrogen partial pressure, from 0.1 to 5 MPa, preferably from 0.2 to 3 MPa.

The solvent used in the present invention is not particularly limited insofar as it does not affect the reduction reaction. For example, the solvent is a sole or combined solvent containing at least one member selected from aromatic hydrocarbons such as benzene, toluene, xylene and ethylbenzene; aliphatic hydrocarbons such as hexane and cyclohexane; alcohols such as methanol, ethanol, propanol, butanol, ethylene glycol, propylene glycol, glycerin and ethylene glycol methyl ether; ethers such as tetrahydrofuran, dioxane and dioxolane; esters such as ethyl acetate and butyl acetate; and water. Among these, preferred are water alone and a combined solvent of water and a solvent which is not completely miscible with water. The solvent which is not completely miscible with water is a solvent such that when mixed with water at least in a certain ratio, separation into two layers occurs. Examples thereof include aromatic hydrocarbons such as toluene, xylene and ethylbenzene, and esters such as ethyl acetate and butylacetate. This combined solvent system is expected to provide an effect of, when the reaction substrate has low solubility in water, allowing the organic solvent to dissolve the substrate in the organic solvent phase and thereby increasing the reaction rate. At this time, when water is simultaneously used, an effect of transferring the resulting amines to the aqueous layer as an organic acid salt and thereby preventing a side reaction (a reaction of amine with nitrile to form a polymer or a substitution reaction of halogen with amine) can be expected.

The amount of the solvent used is not particularly limited but is preferably from 2 to 20 times in mass based on the halogenated aromatic nitrile represented by formula (1).

In the present invention, the reaction temperature is from room temperature to 100° C., preferably from room temperature to 60° C. The pressure is, in terms of the hydrogen partial pressure, from 0.1 to 5 MPa, preferably from 0.2 to 3 MPa. The hydrogen gas for use in the reaction of the present invention needs not be necessarily a high-purity gas and may contain an inert gas having no particular effect on the reduction reaction.

The reaction form is not particularly limited, however, a method such as catalyst suspension flow system, fixed bed flow system, trickle bed or batch system is preferably used.

After the catalyst is separated from the reaction solution by filtration or the like and the residue is neutralized, the halogenated aromatic methylamine represented by formula (2) obtained according to the production process of the present invention can be isolated using a usual isolation method such as condensation, extraction or distillation.

EXAMPLES

The present invention is described below by referring to Examples.

Condition of gas chromatography adopted in the examples is as follows.
<Condition of Gas Chromatography Analysis>
Apparatus: HP6850 manufactured by Hewlett-Packard
Column: DB1701, 0.32 mm×30 m, membrane thickness 0.25 μm
Carrier gas: He
Flow rate: 1.2 ml/min. (constant flow), split ratio 50
Detector: FID
Inj. Temp.: 300° C.
Det. Temp.: 300° C.
Analysis Temp.: 100° C.(5 min.)–10° C./min.->150° C.(10 min.)–15° C./min.->280° C.(5 min.)
Internal standard: 1,4-butane-diol Example 1

Into a 100 cc-volume autoclave, 20 g of water, 10 g of toluene, 2.0 g of sponge nickel catalyst, 3.0 g of acetic acid and 4.0 g of tetrafluoroterephthalonitrile were charged. After purging with nitrogen, the reaction system was thoroughly purged with hydrogen gas to a pressure of 0.85 MPa (gauge pressure) The stirring and heating of the autoclave were started. While maintaining the pressure at 0.85 MPa, hydrogen was continuously supplied and the stirring was continued at 40° C. The amount of hydrogen absorbed was monitored by a mass flowmeter and when the absorption of hydrogen stopped, the reaction was finished. The resulting reaction solution was analyzed by a gas chromatography internal standard method, as a result, the conversion of tetrafluoroterephthalonitrile was 99% or more and the yield of 2,3,5,6-tetrafluoroxylylenediamine was 83%.

The resulting product was confirmed by gas chromatography mass analysis.

Example 2

The same operation as in Example 1 was performed except for changing toluene to xylene. The resulting reaction solution was analyzed by a gas chromatography internal standard method, as a result, the conversion of tetrafluoroterephthalonitrile was 99% or more and the yield of 2,3,5,6-tetrafluoroxylylenediamine was 80%.

Example 3

The same operation as in Example 1 was performed except for charging 30 g of water, 2.0 g of sponge nickel catalyst, 3.0 g of acetic acid and 4.0 g of tetrafluoroterephthalonitrile into a 100 cc-volume autoclave. The resulting reaction solution was analyzed by a gas chromatography internal standard method, as a result, the conversion of tetrafluoroterephthalonitrile was 99% or more and the yield of 2,3,5,6-tetrafluoroxylylenediamine was 90%.

Example 4

The same operation as in Example 1 was performed except for charging 200 g of water, 12.5 g of sponge nickel catalyst, 37.5 g of acetic acid and 50.0 g of tetrafluoroterephthalonitrile into a 500 cc-volume autoclave. The resulting reaction solution was analyzed by a gas chromatography internal standard method, as a result, the conversion of tetrafluoroterephthalonitrile was 99% or more and the yield of 2,3,5,6-tetrafluoroxylylenediamine was 95%.

To the resulting reaction solution, was added 30 wt % of sodium hydroxide aqueous solution to adjust pH so as to be 12.3. After separating an insoluble portion by filtration, water phase was washed with 30 g of toluene. After separating the toluene phase, water phase was extracted three times with the use of 300 g of ethyl acetate. Whole ethyl acetate phase was distilled off under reduced pressure, thereby obtaining 42.8 g of 2,3,5,6-tetrafluoroxylylenediamine as the fraction under 5 mmHg at 120° C. Recovery was 86.8%.

Example 5

Into a 500 cc-volume autoclave, 100 cc of water and 10.0 g of sponge nickel catalyst were charged, and hydrogen pressure was set to be 0.5 MPa at 15° C. The stirring of the autoclave was started, and continuing the stirring for 1 hour while keeping the temperature at 15° C. To the autoclave, were further charged 100 cc of water, 37.5 g of acetic acid and 50.0 g of tetrafluoroterephthalonitrile, then, procedure of Example 1 was repeated. The resulting reaction solution was analyzed by a gas chromatography internal standard method, as a result, the conversion of tetrafluoroterephthalonitrile was 99% or more and the yield of 2,3,5,6-tetrafluoroxylylenediamine was 94%.

Then, the same isolation procedure as in Example 4 was repeated, to thereby obtaining 42.4 g of 2,3,5,6-tetrafluoroxylylenediamine. Recovery was 86.8%.

Example 6

The same operation as in Example 4 was performed except for using 12.5 g of sponge nickel catalyst added with molybdenum. The resulting reaction solution was analyzed by a gas chromatography internal standard method, as a result, the conversion of tetrafluoroterephthalonitrile was 99% or more and the yield of 2,3,5,6-tetrafluoroxylylenediamine was 96%.

Then, the same isolation procedure as in Example 4 was repeated, to thereby obtaining 43.4 g of 2,3,5,6-tetrafluoroxylylenediamine. Recovery was 87.0%.

Comparative Example

The same operation as in Example 4 was performed except for using 37.5 g sulfuric acid in place of acetic acid.

The resulting reaction solution was analyzed by a gas chromatography internal standard method, as a result, the conversion of tetrafluoroterephthalonitrile was 23% and the yield of 2,3,5,6-tetrafluoroxylylenediamine was 12%.

Effect of the Invention

According to the present invention, the halogenated aromatic methylamine represented by formula (2) can be produced in a high yield by an industrially advantageous method.

What is claimed is:

1. A process for producing a halogenated aromatic methylamine, comprising hydrogen-reducing a halogenated aromatic nitrile represented by formula (1):

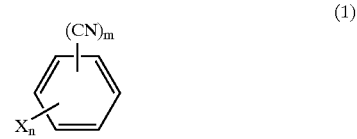

(1)

(wherein X represents a chlorine atom or a fluorine atom, m represents an integer of 1 to 5, n represents an integer of 1 to 5, m+n≦6, and when n is 2 or more, each X may be the same or different) using a hydrogenating catalyst in the presence of an organic acid in a solvent to produce a halogenated aromatic methylamine represented by formula (2):

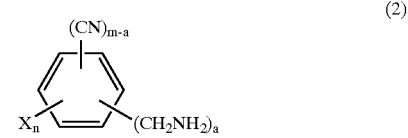

(2)

(wherein X, m and n have the same meanings as defined above, and a represents an integer of 1 to m), and wherein the organic acid is at least one member selected from the group consisting of formic acid, acetic acid and propionic acid.

2. The production process for a halogenated aromatic methylamine as claimed in claim 1, wherein the halogenated aromatic nitrile represented by formula (1) is tetrafluoroterephthalonitrile or tetrafluoroisophthalonitrile and the halogenated aromatic methylamine represented by formula (2) is 2,3,5,6-tetrafluoroxylylenediamine or 2,3,4,6-tetrafluoroxylylenediamine.

3. The production process for a halogenated aromatic methylamine as claimed in claim 1 or 2, wherein the solvent is a sole or combined solvent containing at least one member selected from the group consisting of aromatic hydrocarbons, aliphatic hydrocarbons, alcohols, ethers, esters and water.

4. The production process for a halogenated aromatic methylamine as claimed in claim 1 or 2, wherein the solvent is a sole or combined solvent containing at least one member selected from the group consisting of benzene, toluene, xylene, ethylbenzene, hexane, cyclohexane, methanol, ethanol, propanol, tetrahydrofuran, dioxane, dioxolane, ethyl acetate and water.

5. The production process for a halogenated aromatic methylamine as claimed in claim 3, wherein the solvent is a combined solvent of water and an organic solvent which is not completely miscible with water.

6. The production process for a halogenated aromatic methylamine as claimed in claim 5, wherein the organic solvent which is not completely miscible with water is an aromatic hydrocarbon.

7. The production process for a halogenated aromatic methylamine as claimed in claim 6, wherein the aromatic hydrocarbon is toluene, xylene or ethylbenzene.

8. The production process for a halogenated aromatic methylamine as claimed in claim 1 or 2, wherein the solvent is water.

9. The production process for a halogenated aromatic methylamine as claimed in claim 1, wherein the catalyst contains at least one metal selected from the group consisting of nickel, palladium, platinum, ruthenium, cobalt and copper.

10. The production process for a halogenated aromatic methylamine as claimed in claim 1, wherein the catalyst is sponge nickel or sponge cobalt.

11. The production process for a halogenated aromatic methylamine as claimed in claim 10, wherein the catalyst is sponge nickel.

12. The production process for a halogenated aromatic methylamine as claimed in claim 11, wherein the sponge nickel is modified with metal other than nickel.

13. The production process for a halogenated aromatic methylamine as claimed in claim 12, wherein the sponge nickel is modified with molybdenum.

14. The production process for a halogenated aromatic methylamine as claimed in claim 1, wherein the catalyst is used after pre-treatment in solvent under hydrogen atmosphere at 40° C. or less.

15. The production process for a halogenated aromatic methylamine as claimed in claim 1, wherein the catalyst is supported palladium.

16. The production process for a halogenated aromatic methylamine as claimed in claim 1, wherein the amount of the solvent used is from 1 to 20 times in mass based on the halogenated aromatic nitrile.

17. The production process for a halogenated aromatic methylamine as claimed in claim 1, wherein the amount of the organic acid used is from 50 to 500 mol % based on the nitrile group of the halogenated aromatic nitrile.

18. The production process for a halogenated aromatic methylamine as claimed in claim 1 wherein the amount of the catalyst used is from 0.01 to 1 times in mass based on the halogenated aromatic nitrile.

19. The production process for a halogenated aromatic methylamine as claimed in claim 1, wherein the hydrogen reduction is performed at a reaction temperature of room temperature to 100° C. under a hydrogen partial pressure of 0.1 to 5 MPa.

* * * * *